(12) United States Patent
Duan

(10) Patent No.: US 8,554,317 B2
(45) Date of Patent: Oct. 8, 2013

(54) MICRONEEDLE ARRAYS AND METHODS OF USE THEREOF

(75) Inventor: Daniel C. Duan, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 941 days.

(21) Appl. No.: 12/090,422

(22) PCT Filed: Nov. 16, 2006

(86) PCT No.: PCT/US2006/044492
§ 371 (c)(1),
(2), (4) Date: Apr. 16, 2008

(87) PCT Pub. No.: WO2007/064486
PCT Pub. Date: Jun. 7, 2007

(65) Prior Publication Data
US 2008/0287858 A1     Nov. 20, 2008

Related U.S. Application Data

(60) Provisional application No. 60/741,096, filed on Nov. 30, 2005.

(51) Int. Cl.
*A61N 1/30* (2006.01)
(52) U.S. Cl.
USPC .............................. 604/21; 604/65
(58) Field of Classification Search
USPC ................... 604/103.1, 529, 21, 65
See application file for complete search history.

(56) References Cited

U.S. PATENT DOCUMENTS

| | | |
|---|---|---|
| 6,293,925 B1 | 9/2001 | Safabash et al. |
| 6,334,856 B1 | 1/2002 | Allen et al. |
| 6,611,707 B1 | 8/2003 | Prausnitz et al. |
| 6,743,211 B1 | 6/2004 | Prausnitz et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 2002/0032415 A1 | 3/2002 | Trautman et al. |
| 2002/0087182 A1 | 7/2002 | Trautman et al. |
| 2002/0123675 A1 | 9/2002 | Trautman et al. |

(Continued)

FOREIGN PATENT DOCUMENTS

| | | |
|---|---|---|
| JP | 2003-004639 | 1/2003 |
| WO | WO 2006/055799 | 5/2006 |
| WO | WO 2006/055844 | 5/2006 |

OTHER PUBLICATIONS

Cormier. Journal of Controlled Release 97, 3, (2004) 503-511.

(Continued)

*Primary Examiner* — Kevin C Sirmons
*Assistant Examiner* — Brandy S Lee

(57) ABSTRACT

A method of treating a patient with a microneedle array having an active agent disposed on at least a portion of one or more of the microneedles, wherein the array with active agent is characterized by a first optical response when probed with a selected incident light spectrum. The array with active agent is applied to a skin surface, optionally allowed to remain on the skin surface for a specified time, and removed. The used array is probed with the selected incident light spectrum, a second optical response is sensed, and the difference between the first optical response and the second optical response is determined and compared to a predetermined threshold value.

7 Claims, 2 Drawing Sheets

(56) References Cited

U.S. PATENT DOCUMENTS

| | | |
|---|---|---|
| 2002/0128599 A1 | 9/2002 | Cormier et al. |
| 2002/0193729 A1 | 12/2002 | Cormier et al. |
| 2003/0045837 A1 | 3/2003 | Delmore et al. |
| 2003/0093040 A1 | 5/2003 | Mikszta et al. |
| 2003/0095582 A1 | 5/2003 | Ackley |
| 2003/0135166 A1 | 7/2003 | Gonnelli |
| 2003/0143113 A2 | 7/2003 | Yuzhakov et al. |
| 2003/0208113 A1 | 11/2003 | Mault et al. |
| 2004/0049150 A1 | 3/2004 | Dalton et al. |
| 2004/0062813 A1 | 4/2004 | Cormier et al. |
| 2004/0077994 A1 | 4/2004 | Lastovich et al. |
| 2004/0082934 A1 | 4/2004 | Pettis |
| 2004/0181203 A1 | 9/2004 | Cormier et al. |
| 2004/0254559 A1* | 12/2004 | Tanaami et al. .............. 604/403 |
| 2004/0265354 A1* | 12/2004 | Ameri et al. .................. 424/423 |
| 2004/0265365 A1 | 12/2004 | Daddona et al. |
| 2005/0100937 A1 | 5/2005 | Holmes |
| 2005/0137525 A1 | 6/2005 | Wang et al. |
| 2005/0153873 A1 | 7/2005 | Chan et al. |
| 2005/0261631 A1 | 11/2005 | Clarke et al. |
| 2006/0036209 A1 | 2/2006 | Subramony et al. |

OTHER PUBLICATIONS

Wildera. Effect of delivery parameters on immunization to ovalbumin following intracutaneous administration by a coated microneedle array patch system. Vaccine. 24(10): 1653-1664. Oct. 6, 2005.

Xie. Controlled transdermal delivery of model drug compounds by MEMS microneedle array. Nanomedicine. 1(1): 184-190. Jun. 2005.

Watson. Intracellular trafficking pathways and drug delivery: fluorescence imaging of living and fixed cells. Adv Drug Deliv. Rev. 57(1):43-61. Jan. 2, 2005.

* cited by examiner

MICRONEEDLE ARRAYS AND METHODS OF USE THEREOF

CROSS REFERENCE TO RELATED APPLICATIONS

This application is a national stage filing under 35 U.S.C. 371 of PCT/US2006/044492, filed Nov. 16, 2006, which claims priority to Application No. 60/741,096, filed Nov. 30, 2005, the disclosure of which is incorporated by reference in its/their entirety herein.

FIELD

The present invention relates to microneedle arrays and methods of use of microneedle arrays.

BACKGROUND

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

In one approach, a delivery device comprises an active agent that is externally coated onto an array of microneedles and the active agent is delivered directly into the skin after the microneedles breach the stratum corneum. A number of mechanisms may cause the active agent to be removed from the microneedles and deposited in the skin. For example, the active agent may dissolve off of the microneedles when in contact with interstitial fluid. In certain instances the microneedles may be left in contact with the skin for a specified period of time in order to allow sufficient delivery of the active agent.

SUMMARY OF THE INVENTION

Microneedles are quite small and are thus not readily visible to the naked eye. In addition, a dried coating of an active agent on a microneedle represents a very small amount of material. The ability to distinguish between a microneedle array with and without an active agent coating is thus generally not possible by unaided visual observation. It would be desirable to be able to confirm that the active agent of a delivery device has indeed been delivered into the skin after the delivery device has been applied and subsequently removed from a patient In a first aspect, the present invention is a method of treating a patient with a microneedle array having an active agent disposed on at least a portion of one or more of the microneedles, wherein the array with active agent is characterized by a first optical response when probed with a selected incident light spectrum. The array with active agent is applied to a skin surface, optionally allowed to remain on the skin surface for a specified time, and removed. The used array is probed with the selected incident light spectrum, a second optical response is sensed, and the difference between the first optical response and the second optical response is determined and compared to a predetermined threshold value.

In a second aspect, the present invention is a drug delivery device comprising a plurality of microneedles arranged on a substrate, each microneedle having a base and a tip. The tip of one or more of the microneedles has a first optical response when probed with a selected incident light spectrum and the base of the microneedle has a second optical response when probed with the selected incident light spectrum, the second optical response differing from the first optical response. An active agent formulation covers at least a portion of the tip of one or more of the microneedles and modulates the first optical response of the microneedles when probed with the selected incident light spectrum.

In a third aspect, the present invention is a microneedle array comprising a plurality of tapered microneedles arranged on a substrate, wherein the microneedles have a fluorescence that is greater than that of the substrate.

In a fourth aspect, the present invention is a measurement device for determining if an active agent is successfully delivered from a microneedle array wherein the array with active agent is characterized by a first optical response when probed with a selected incident light spectrum. The measurement device comprises: a holder configured to receive and orient the microneedle array; a light source aligned so as to probe the received and oriented microneedle array with the selected incident light spectrum; a detector aligned so as to detect a second optical response of the microneedle array in response to the probing with the selected incident light spectrum; an analysis device that analyzes whether the difference between the first optical response and the second optical response exceeds a predetermined threshold value; and a signaling device that generates a signal in response to the determination of the difference between the first optical response and the second optical response.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," or "microneedle" refers to the specific microscopic structures associated with the array, also referred to as a "microarray", that are capable of piercing the stratum corneum to facilitate the transdermal or intradermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein.

Figure 1:
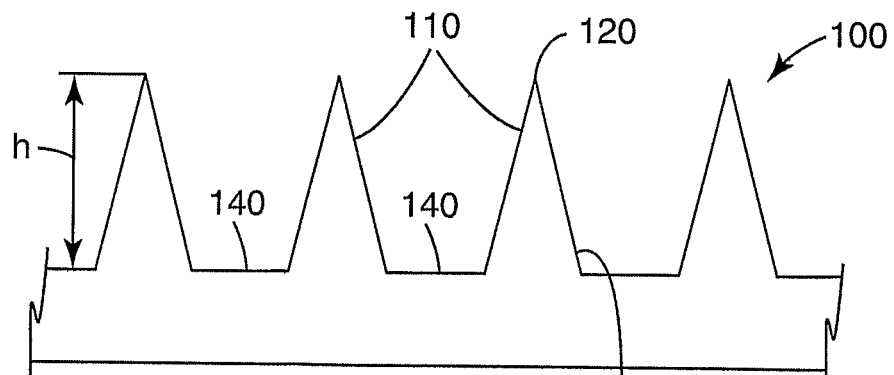
FIG. 1 is a schematic side view of a portion of a microneedle array.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers may be used throughout the figures to denote like parts.

DETAILED DESCRIPTION

One embodiment of the present invention is a method of treating a patient with a device comprising a microneedle array with an active agent. The microneedle array has an active agent formulation disposed on at least a portion of the microneedles. The active agent formulation may take a variety of forms, such as a solid, gel, hydrogel, powder, liquid, viscous fluid, or adhesive. The active agent formulation is preferably a solid or powder. The active agent formulation may take on any of a number of different shapes, such as a thin laminar coating, a single droplet shape on the tip of the microneedle, or a plurality of discrete particles adhered to the sides of the microneedles. The active agent formulation may be preferentially located near the tips of the microneedles or it may be dispersed along the entire surface of the microneedles. The active agent formulation may also reside on the substrate. In one embodiment the concentration or amount of active agent on the substrate is less than that on the microneedles. In one embodiment, the active agent formulation is present as a thin coating or layer on the external surface of the microneedles. Such a coating or layer may vary in thickness, and in some instances may range from about 1 micron to about 100 microns thick.

The microneedle array with active agent formulation is characterized by having a first optical response when probed with a selected incident light spectrum. The incident light spectrum may be broadly considered to be any combination of wavelengths of electromagnetic radiation in the ultraviolet, visible, and/or infrared regions of the electromagnetic spectrum. For purposes of definition, the ultraviolet region is considered to include wavelengths ranging from about 100 to about 400 nm, the visible region about 400 to about 800 nm, and the infrared region about 800 nm to about 1000 microns. In one embodiment, suitable infrared radiation may be in the near-IR range, that is, about 800 nm to about 1 micron, and/or in the mid-IR range, that is, about 2.5 to about 15 micron.

The optical response will most typically comprise absorption or absorbance, reflection, scattering, fluorescence, and/or phosphorescence. In one embodiment the optical response is fluorescence. In one embodiment the optical response is absorption. A selected incident light spectrum may elicit a variety of optical responses from the microneedle array and/or active agent formulation. In one embodiment, a single optical response will be monitored. For example, the optical response may be the intensity of a particular wavelength indicative of fluorescence.

The microneedle array with active agent is applied to a skin surface in order to deliver the active agent to a patient. The array may be removed immediately after application or optionally left in place on the skin surface for a specified time. It may be desirable to leave the array in place for a given or specified time period (e.g., 1 minute, 5 minutes, more than 5 minutes, 20 minutes) to allow time for at least a portion of the active agent formulation to deposit into or be taken up into the skin. For example, the active agent formulation may be a solid adhered to the microneedles and require some time to dissolve into the interstitial fluid in the skin.

In one embodiment, an applicator device may be used to apply the array to the skin surface. Such an applicator may control various application parameters, such as the speed with which the array is applied, the force with which the array is applied, and/or the angle with which the array impacts the skin. In addition, an applicator may aid in handling or otherwise transferring the array from a storage unit to the patient. In one embodiment, the applicator may be a single-use, disposable device that serves as both a storage unit and an application device. Examples of suitable applicators and methods of application of microneedle arrays are disclosed in U.S. Pat. Nos. 6,293,925 (Safabash et al.), 6,743,211 (Prausnitz et al.), 6,881,203 (Delmore et al.), and 6,855,131 (Trautman et al.), and United States Patent Application Publication Nos. 2004/0181203 (Cormier et al.), 2002/0032415 (Trautman et al.), and 2002/0087182 (Trautman et al.), the disclosures of which are herein incorporated by reference.

After removing the array from the patient it is probed with the selected incident light spectrum to elicit a second optical response. This optical response will be of the same type as the first optical response (e.g., if the first optical response is a wavelength indicative of fluorescence, then the same wavelength will be monitored for the second optical response). The second optical response is sensed and if a sufficient portion of the active agent formulation is delivered from the array, then the second optical response will differ in intensity from the first optical response. The change in optical response versus the amount of active agent formulation removed from the microneedles may be calibrated and a predetermined threshold value of the difference between first and second optical responses can be established based on the desired amount of active agent to be delivered. It should be understood that the first optical response will typically have a known and constant value based on various manufacturing parameters. Thus, in use, a measurement device may only need to measure the second optical response and compare this to the known (but not directly measured by the measurement device) first optical response.

Figure 2:
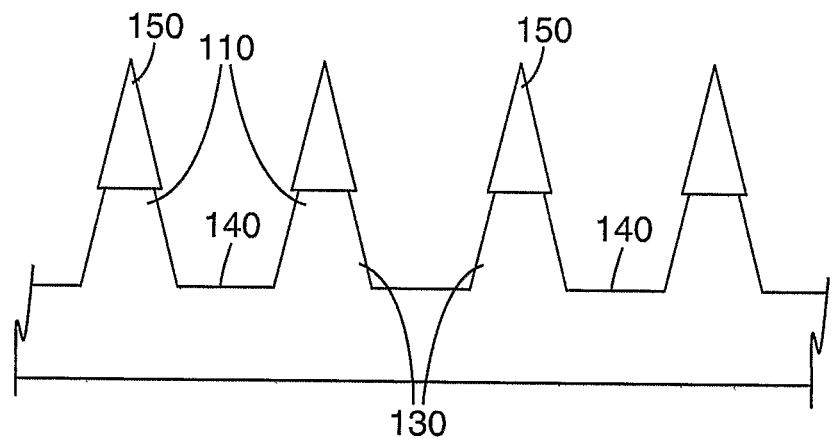
FIG. 2 is a schematic side view of a portion of a microneedle array with an active agent formulation coating.

In one embodiment, as shown in FIGS. 1 and 2, the microneedle array 100 (only a portion of which is shown) comprises microneedles 110 having upper tip portions 120 that fluoresce in response to incident ultraviolet or visible light and lower base portions 130 that are substantially non-fluorescent to the same incident ultraviolet or visible light. The substrate 140 is also substantially non-fluorescent to the same incident ultraviolet or visible light. The active agent formulation 150 is applied as a dried coating that covers the fluorescent upper tip portions. In one embodiment, the active agent formulation absorbs at least a portion of the incident ultraviolet or visible light and thus prevents it from reaching the tip portions of the microneedles. In one embodiment, the active agent formulation absorbs fluorescent light emitted by the tip portions of the microneedles and thus prevents at least a portion of it from reaching a detector. In one embodiment, the active agent formulation may both absorb incident ultraviolet or visible light and emitted fluorescent light. Thus, an unused microneedle array, that is, a microneedle array with a full dose of active agent, will present little or no fluorescent light in response to the incident ultraviolet or visible light. If the active agent is delivered to the patient, that is, it is removed from the array, then the fluorescent tip portions of the microneedles will present a fluorescent response with increased intensity. The intensity of the fluorescent response may be calibrated as a function of active agent formulation on the array in order to determine how much active agent formulation has been removed from the array during use.

The microneedles 110 may be characterized by a height, h, which is measured from the plane of the substrate to the tip of the needle as shown in FIG. 1. In one embodiment, the tip portion 120 is the portion of the needle between the tip and the halfway point along the height of the needle, that is, the portion of the needle at least 0.5*h above the substrate. In another embodiment, the tip portion 120 is the portion of the needle at least 0.75*h above the substrate and sometimes 0.90*h above the substrate. The base portion 130 is the remainder of the needle that is not the tip portion 120. In one embodiment, at least a part of the tip portion 120 and the base portion 130 may be made from different materials. In particular, it may be desirable for the tip portion 120 and the base portion 130 of each needle to present a different response when probed with an incident light spectrum. In one embodiment, the base portion 130 will present little or no response when probed with an incident light spectrum. In one embodiment, the tip portion 120 will present a positive response when probed with an incident light spectrum. In one embodiment, the tip and base portions are made entirely from two different materials. In another embodiment, part of the tip may comprise a first material that is the same as the material of the base portion, but the tip portion may also have a second material, such as a fluorescent dye, dissolved or dispersed within the first material. Such a second material may be homogeneously mixed throughout the tip portion, it may be concentrated in particular parts of the tip portion, such as near the outer surfaces of the tip portion, or it may be an external layer or coating on the tip portion. Microneedles where the tip and base portions comprise different materials may be made by any of a number of means. A two-part molding process, for instance, may be suitable for making microneedles with differing tip and base portions. Alternatively, an inner portion of the microneedle may be molded and then one or more external layers may be coated onto the inner portion of the microneedle. Such a coating may be applied directly as a dried material or coated from a carrier solvent, which is subsequently allowed to evaporate. U.S. patent application Ser. Nos. 60/629,187 and 60/629,209, the disclosures of which are incorporated by reference, provide examples of suitable techniques for coating microneedles.

Figure 3:
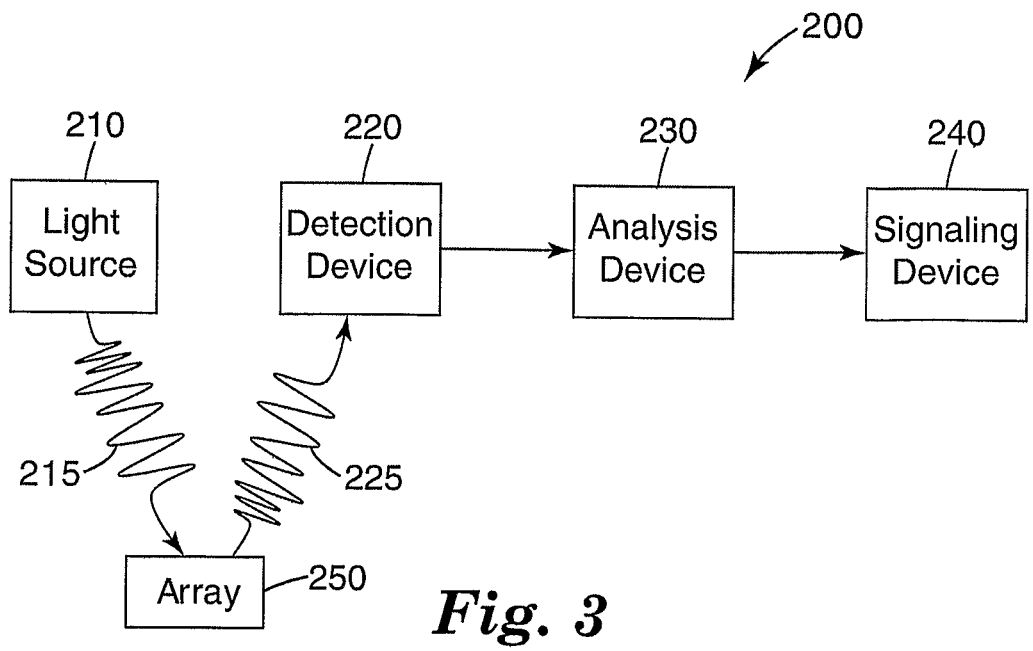
FIG. 3 is a block diagram of a measurement device.

In one embodiment, a measurement device 200 is used to perform the steps of probing, detecting, analyzing, and signaling. After removing the array from the patient, a light source 210 is used to probe the array 250 with the selected incident light spectrum 215 to elicit a second optical response 225 which is detected by a detection device 220, as shown schematically in FIG. 3. This optical response 225 will be of the same type as the first optical response (e.g., if the first optical response is a wavelength indicative of fluorescence, then the same wavelength will be monitored for the second optical response). If a sufficient portion of the active agent formulation is delivered, and thus removed from the microneedle array 250, then the second optical response 225 will differ from the first optical response. The change in optical response versus the amount of active agent formulation removed from the microneedles may be determined with an analysis device 230. The second optical response will often be recorded or converted to a digital input, which a conventional analysis device, such as a computer, may compare to the first optical response. The system may be calibrated to establish a predetermined threshold value of the difference between first and second optical responses which can be based on the desired amount of active agent to be delivered. A signaling device 240 may be used to indicate if the active agent was successfully delivered. The signaling device may be any sort of conventional indicator, for example, a light, audible tone, or a digital readout, and will typically provide a signal in response to the determination of the difference between the first optical response and the second optical response.

Figure 4:
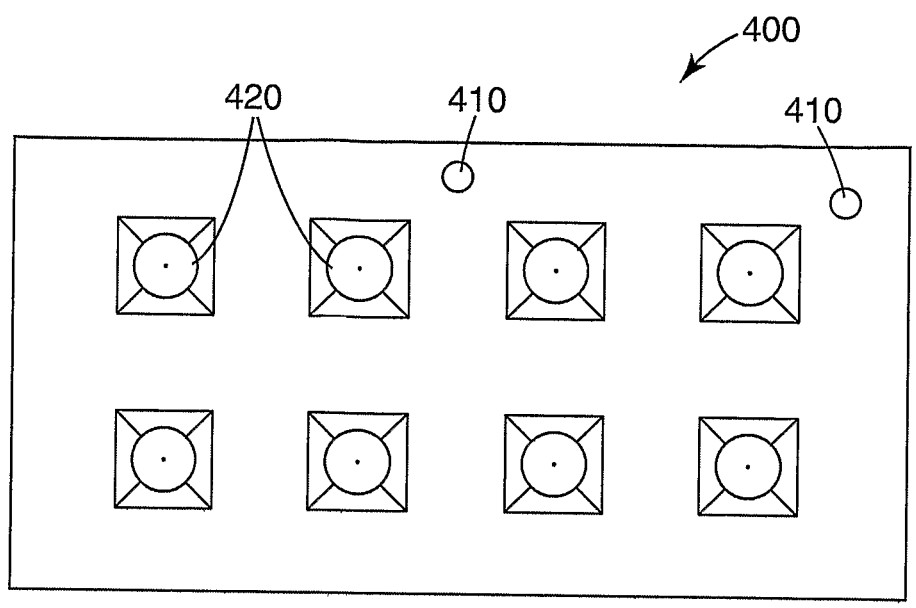
FIG. 4 is a schematic top view of a portion of a microneedle array.

It is envisioned that a small hand held measurement device would be suitable for making measurements of microneedle arrays to determine the presence or absence of active agent coating. The array with active agent will typically come as a pre-packaged unit and as such should contain a full dose. However, a health care provider could easily confirm this by making a measurement of an unused array. In the embodiment described above, an unused array would present little or no fluorescent signal, thus confirming the presence of the active agent. One or more optional indicators could be added to the array to confirm that the measurement device is working properly. For example, one or more fluorescent spots 410 as shown in FIG. 4 could be placed at locations on the array 400 where there is no active agent formulation, so that measurement of an unused array provides a small confirming signal that the measurement device is working properly. The active agent formulation 420 is shown covering the tips of the microneedles, thus blocking some or all of the fluorescence of the tips. This may be desirable, since the mere absence of a signal might possibly be due to a malfunction in the sensor device.

After application, the used array may be inserted (or re-inserted) into a holder (e.g., a slot or tray) within the measurement device and probed with the selected incident light spectrum. An increased fluorescent signal could be used directly as a visual indicator to confirm removal of the active agent from the microneedles or it could be detected with a detection device, analyzed, and used to trigger a signaling device, for example, a visible or audible indicator, if the measurement exceeded a predetermined threshold value. In one embodiment a single external action may trigger the steps of probing, detecting, analyzing, and signaling. Examples of suitable external actions include pushing a button, turning a knob, or moving a lever. Alternatively, the measurement device may be configured such that insertion of a used microneedle array into the device triggers one or more of the steps of probing, detecting, analyzing, and signaling. In one embodiment, the analysis device and the detection device may be integrated into a single measuring system.

Although the general description above is illustrated with an embodiment comprising microneedles with fluorescent tips, the method of treatment of the present invention may be accomplished in numerous other ways. The entire array could be fluorescent and the difference between the first and second optical responses would be indicative of an increase in intensity of the second response due to a greater exposed surface area of the array if the active agent formulation is removed. Thus an unused array would provide a response with a baseline intensity and this response would increase after removal of the active agent formulation. In one embodiment, the baseline response is minimized or is preferably substantially negligible. This may be done by preparing a microneedle array having a fluorescent response only in the areas of the array that are covered by active agent formulation. Thus if the microneedles are completely covered by active agent formulation, but the substrate is uncovered, then the microneedles would be fluorescent, but the substrate would not be fluorescent. A substantially negligible response would be equal to or less than the standard error in the positive response measurement. That is, it would be the same intensity or less than the noise level in the positive response, so it would have no significant effect on the quality of the positive response signal.

In one embodiment, the active agent formulation could have a fluorescent response and the microneedle array would be non-fluorescent. Thus, a used array would show a marked decrease in fluorescent intensity in comparison to an unused array.

In one embodiment, the optical response could be absorbance. For example, the array could be formed from a black or dark material in contrast with a lightly colored active agent formulation. Thus, in response to incident light in the visible spectrum, an unused array would present a strong response due to diffuse reflectance. Removal of the active agent formulation would cause the response to drop significantly in intensity. Alternatively, a dark colored or highly absorbent active agent formulation could be used to cover a light colored array. As discussed above, the light colored array would provide a response with a baseline intensity even in, the presence of the active agent formulation, but this response would increase when the active agent was removed. In another alternative, the array could have a specific color which would be partially or totally blocked by the active agent formulation. Detection and analysis could be performed using an automated measurement device sensitive to an appropriate wavelength of light. Alternatively, detection could be performed by visual inspection and comparison to a standard color chart, for example, to indicate if the dose had been removed from the array. In still another alternative, the array could be substantially transparent and the active agent formulation would absorb a portion of the incident light spectrum. A measurement of the transmitted light would thus distinguish between arrays with and without active agent formulation.

In still another embodiment, an image analysis system could detect contrasting features presented by the active agent formulation coating on the array. For example, the active agent formulation might be detected as dots or spots on the surface of the microneedles. Disappearance of these features would indicate removal of the active agent formulation and could be quantified by a reduction in the number and/or the size of the contrasting features. Image analysis may be employed with any suitable first optical response, such as those described above.

In one embodiment, the optical response could be reflectance. A shiny metal array could be entirely covered by an active agent formulation, and thus provide little or no reflectance prior to use. Removal of the active agent formulation would expose part or all of the shiny metal array and cause an increase in the amount of reflected light. The array could also be selectively reflective to match the areas of the array covered by the active agent formulation. For example, a metal array could have an anodized or black substrate and an active agent formulation covering the entire surface of the microneedles. Thus an unused array would provide little or no reflectance, but removal of the active agent formulation would expose the shiny metal microneedles and cause a strong response to the incident light spectrum.

Light emitted at any angle from the array may be suitable as the detected response. For example, the illumination and detection responses could travel along substantially the same path, that is, where the light emitting from the array in response to the illuminating radiation re-traces the path of the illuminating radiation. In such an instance, the light source and detection device may be co-located. Alternatively, the light emitting from the array may be detected at an acute angle, a right angle, or an obtuse angle from the incident illumination. In a further alternative, light that is transmitted directly through the array could be detected (i.e., light emitted at an angle of 180 degrees to the incident light). In one embodiment, multiple detectors or a single detector having multiple, spatially separated sensing portions may be used to detect a response at a plurality of angles.

Figure 5:
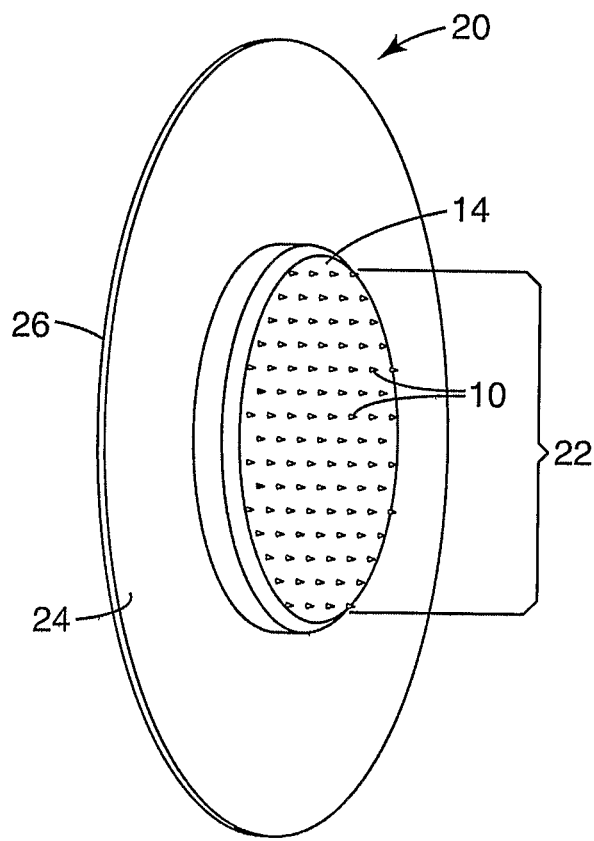
FIG. 5 is a schematic perspective view of a microneedle device.

In one embodiment, the microneedle array shown schematically as 100 in FIG. 1 may be part of a larger device in the form of a patch shown in FIG. 5. FIG. 5 illustrates a microneedle device comprising a patch 20 in the form of a combination of an array 22, pressure sensitive adhesive 24 and backing 26. The array 22 is illustrated with microneedles 10 protruding from a microneedle substrate surface 14. The microneedles 10 may be arranged in any desired pattern or distributed over the microneedle substrate surface 14 randomly. As shown, the microneedles 10 are arranged in uniformly spaced rows. In one embodiment, the array may have a skin-facing surface area of more than about 0.1 cm$^2$ and sometimes more than about 0.5 cm$^2$. In one embodiment, the array may have a skin-facing surface area of less than about 20 cm$^2$ and sometimes less than about 5 cm$^2$. In one embodiment, the array may have a skin-facing surface area of between about 0.5 cm$^2$ and about 5 cm$^2$. In one embodiment (not shown), a portion of the substrate surface 14 of the patch 20 is non-patterned. In one embodiment the non-patterned surface has an area of more than about 1 percent and less than about 75 percent of the total area of the device surface that faces a skin surface of a patient. In one embodiment the non-patterned surface has an area of more than about 0.10 square inch (0.65 cm$^2$) to less than about 1 square inch (6.5 cm$^2$). In another embodiment (shown in FIG. 5), the microneedles are disposed over substantially the entire surface area of the array 22.

The microneedle devices useful in the various embodiments of the invention may comprise any of a variety of configurations, such as those described in the following patents and patent applications, the disclosures of which are herein incorporated by reference. One embodiment for the microneedle devices comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. In one embodiment, the surface of the channels may be fluorescent and the remainder of the microneedle non-fluorescent. Another embodiment for the microneedle devices comprises the structures disclosed in U.S. Patent Application Publication No. 2005/0261631, which describes microneedles having a truncated tapered shape and a controlled aspect ratio. In one embodiment, the truncated tip of the microneedle may have an optical response, such as fluorescence, that differs from the remainder of the microneedle and substrate. Microneedle devices suitable for use in the present invention may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, inactivated virus particles, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, such as sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing the activity of vaccine adjuvants. Examples of suitable vaccines and vaccine adjuvants are disclosed in United States Patent Application Publication No. 2004/0049150 (Dalton et al.) and No. 2002/0193729 (Cormier et al.), the disclosures of which are herein incorporated by reference.

Microneedle devices may be used for immediate delivery, that is where they are applied and immediately removed from the application site. In one embodiment, it may be desirable to leave the microneedle device in place for a relatively short period of time to allow for more complete delivery of a drug than can be obtained upon application and immediate removal. Such a short period of time is typically less than or equal to about 30 minutes, often less than or equal to about 20 minutes, and sometimes less than or equal to about 5 minutes. In one embodiment, it may be desirable to leave the microneedle device in place for an extended time, which may range from 30 minutes to as long as 1 week.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

I claim:

1. A drug delivery device comprising:
    a plurality of microneedles arranged on a substrate, each microneedle having a base and a tip;
    wherein the tip of one or more of the microneedles has a first optical response when probed with a selected incident light spectrum;
    wherein the base of the microneedle has a second optical response when probed with the selected incident light spectrum, the second optical response differing from the first optical response;
    an active agent formulation covering at least a portion of the tip of one or more of the microneedles; and
    wherein the active agent formulation modulates the first optical response of the microneedles when probed with the selected incident light spectrum.

2. A drug delivery device as claimed in claim 1 wherein the first optical response is selected from the group consisting of absorbance, reflection, scattering, fluorescence, image analysis, and phosphorescence.

3. A drug delivery device as claimed in claim 1 wherein the first optical response is fluorescence.

4. A drug delivery device as claimed in claim 1 wherein the first optical response is absorbance.

5. A drug delivery device as claimed in claim 1 wherein the incident light spectrum comprises visible wavelengths.

6. A drug delivery device as claimed in claim 1 wherein the incident light spectrum comprises ultraviolet wavelengths.

7. A drug delivery device as claimed in claim 1 wherein the active agent formulation prevents a portion of the incident light spectrum from reaching one or more of the microneedles.

* * * * *